United States Patent [19]
Brown

[11] 4,117,845
[45] Oct. 3, 1978

[54] BED URINAL APPARATUS

[76] Inventor: Esther S. Brown, 2000 S. 21st St. East, Salt Lake City, Utah 84108

[21] Appl. No.: 722,730

[22] Filed: Sep. 13, 1976

[51] Int. Cl.[2] .................... A61F 5/44

[52] U.S. Cl. .................... 128/295; 128/2 F; 4/144.1

[58] Field of Search .................... 128/2 F, 295; 4/110, 4/119, 138, 142

[56] References Cited

U.S. PATENT DOCUMENTS

| | | | |
|---|---|---|---|
| 75,658 | 3/1868 | Rensselaer | 4/110 |
| 137,214 | 3/1873 | Knight et al. | 4/110 |
| D. 205,746 | 8/1966 | Cain | 128/295 |
| 2,756,751 | 7/1956 | Smith | 128/295 |
| 2,840,079 | 6/1958 | Conway et al. | 128/295 |

*Primary Examiner*—Robert W. Michell
*Assistant Examiner*—Henry S. Layton
*Attorney, Agent, or Firm*—Trask & Britt

[57] ABSTRACT

A conventional cylindrically shaped bed urinal is modified to include an outlet which is conncted by flexible tubing to a collecting vessel positioned below the bed of a bedridden non-ambulatory male patient. Attachment means such as cloth straps are provided to secure the modified bed pan between the legs of the patient to permit the patient to void his bladder as desired. The bed urinal may be shaped to have concave sides dimensioned to conform to the dimensions of the thighs of the patient.

5 Claims, 2 Drawing Figures

BED URINAL APPARATUS

BACKGROUND OF THE INVENTION

Field

This invention relates to medical apparatus. More particularly, this invention provides for a bed urinal apparatus for use with bedridden non-ambulatory male patients.

State of the Art

Bed urinals for use as urine receptacles for bedribben male patients are well known. Such bed urinals are typically positioned between the legs of bedridden non-ambulatory male patients proximate the thighs to receive urine. After the patient has voided his bladder, the urinal is removed and emptied. In some cases, the patient, by virtue of a disablement, must void frequently and/or has little control over his bladder. In the past and even on occasion today, attending personnel (e.g., nurses, nurse's aides) were sometimes required to expend a substantial amount of time attending to the voiding function of the patient by positioning and thereafter removing and emptying the urinal. The practice today on many occasions, however, is to provide the bedridden non-ambulatory male patient with an installed device to permit the bladder to be voided at will. Typically such devices are urethetic catheters and sheaths or condoms. The urethetic catheter is inserted to receive the urine and connected by a tube to an exterior receptacle such as a jug or similar container. Such catheters are notably uncomfortable, if not painful, and may give rise to bed sores in the general vicinity of the patient's crotch. Sheaths or condoms connected by a tube to a recepticle are perhaps less uncomfortable, but they too contribute to bed sores and to the discomfort of the patient. Further, the male patients, especially male patients in a semiconscious state, absentmindedly or otherwise respond to the discomfort of catheters and condoms or sheaths by moving and acting in a manner that the device eventually becomes dislodged or removed. Bed wetting is a frequent result.

From another view, a bedridden non-ambulatory patient, by virtue of a disablement, may experience discomfort and even pain if he cannot void his bladder as the need arises. Attending personnel such as nurses may not be immediately available to position a urinal to permit the patient to void. As a result, the patient is forced to bear the discomfort. Indeed, on occasion patients have not been able to bear the discomfort or wait. The concomitant results cause additional work in that bed linen must be changed which on occasion hazard the patient's health because of the disruption associated with changing bed linen.

SUMMARY OF THE INVENTION

An apparatus for continuously collecting urine from bedridden non-ambulatory male patients is comprised of an enclosed vessel shaped and dimensioned for placement between the legs of a patient proximate the patient's thighs and attachment meas for securing the vessel to the patient in a position to receive urine from the patient. The vessel has an open end of sufficient cross section to receive the urine of the patient. The open end is positioned with respect to the vessel to form a shoulder inhibiting the flow of liquid out of the vessel when the vessel is placed between the legs of the patient. The vessel also has a closed end opposite the open end and an outlet adapted for connection to a drain tube. When the vessel is positioned between the legs of the patient and secured to the patient by the attachment means, the vessel is oriented to place the outlet at about the natural collection point of liquids within the vessel. The apparatus may further include a collection vessel positioned below the enclosed vessel to receive the urine through a tube which interconnects the collection vessel and the enclosed vessel to permit the gravitional flow of liquids therebetween.

The enclosed vessel preferably has a substantially flat surface which is oblique to the axis of the enclosed vessel and which intersects the closed end of the vessel. The area of the flat surface is sized to stably support the vessel when both empty and full of liquids and when placed on the bed of the patient between the legs of the patient. The outlet is preferably positioned in the closed end at the point near the intersection of the closed end and the base.

The enclosed vessel preferably has opposite concave sides and a top. The concave sides are sized in radius and height to comfortably conform to the dimensions of the thighs of the patient. A handle may be adapted to the top. The attachment means is preferably comprised of cloth straps of sufficient length to encircle the waist of the patient above the hips and means to secure the straps to the enclosed vessel. The collection vessel may be a jug having a neck adapted to receive the tube and having vent means.

The enclosed vessel may also be a conventional cylindrically shaped bed patient urinal of the type having a small cross section mouth and a substantially flat base oblique to the axis of the urinal and intersecting its bottom.

BRIEF DESCRIPTION OF THE DRAWINGS

In the drawings, which illustrate the best mode presently contemplated for carrying out the invention.

DESCRIPTION OF THE ILLUSTRATED EMBODIMENT

Figure 1:
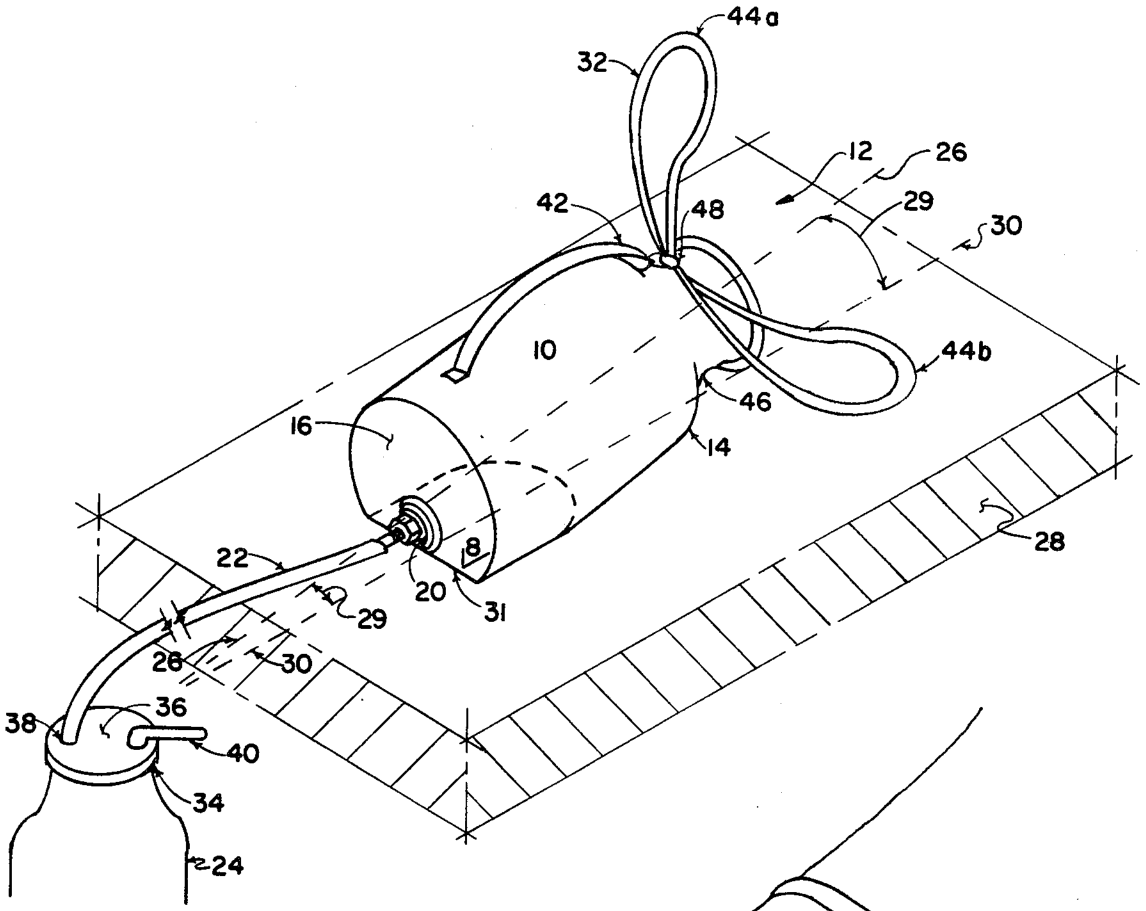
FIG. 1 is a perspective view of a bed pan apparatus of the instant invention.

FIG. 1 depicts a conventional bed urinal 10 having a reduced cross-sectional mouth 12 and a shoulder 14 to inhibit the flow of liquids therefrom when the urinal 10 is positioned for use as hereinafter discussed. The urinal 10 also has a bottom 16 and a base 18. An outlet 20 is formed in the bottom 16 to permit liquids to flow through an interconnecting flexible tube 22 to the collecting vessel 24.

The urinal is substantially symmetrically formed and has a central axis 26. The base 18 is a substantially flat surface which intersects the bottom 16. The base 18 is of sufficient size in area and is oblique to the axis 26 so that the urinal 10 may be placed upon its base 18 on the matrix 28 of the bedridden patient with the mouth 12 extending upward away from the horizontal plane of the mattress 28 as indicated by the angle 29 between the axis and the line 30 in the plane of the mattress 28. The outlet 20 is preferably positioned in the bottom 16 of the urinal 10 near or very close to the intersection of the base 18 with the bottom 16. The natural collecting point for liquids in the urinal with the urinal positioned on the mattress 28 will be in general on the base 18 and in particular along the edge 31 formed by the intersection of the base 18 with the bottom 16. As more particularly set forth hereinafter, when the attachment means 32 are secured to the patient, the urinal 10 should be at a slightly higher angle with respect to the mattress as depicted by the angle 29 between the axis 26 and the plane of the mattress 28 which contains the base line 30 to allow the liquids to more readily collect on the base 18 along the edge 31. With the liquids collecting on the base 18 and preferably along the edge 31 the liquids will flow by gravity out of the outlet 20 and through the flexible tube 22 to the collecting vessel 24 which is preferably an enclosed jar 24 positioned below the mattress 28. The jar 24 is preferably positioned next to or under the bed of the patient out of the way of attending personnel. The jar 24 may have volumetric scribe marks so that the precise volume of voided liquids may be measured for diagnostic purposes when required.

The collecting vessel 24, as hereinbefore noted, is a glass jar having a narrow mouth 34 with a stopper 36 therein having an aperture 38 formed therein to receive the flexible tube 22 and allow liquids to pass into the jar 24. The aperture 38 may be oversized so that it may also act as a vent. Alternately, a separate vent 40 may be formed in the stopper 36. Indeed, in some cases it may be desirable to have a separate vent device containing activated charcoal or other deodorizing means.

The urinal 10 also has a handle 42 preferably positioned generally diametrically opposite the base 18. The handle is convenient for attending personnel to position and remove the urinal. The attachment means as here illustrated are cloth straps **44*a* and 44*b* which are sized in length to pass around the waist of the bedridden male patient just above the hips. The cloth straps may be secured to the handle 42 or around the neck 46 of the urinal 10 using conventional knots 48 as desired by the user. Preferably the straps 44*a* and 44*b* (FIG. 2) are elongated cloth straps which are led over the top of the thighs of a reclining patient, above his hips, around the small of the back at about waist level and back to the front to be secured to each other at waist level by means which as here illustrated are snaps 47**. It should be understood, however, that other attachment means may be used including tape, velcro strips or elastic straps to provide a greater securing tension when the need arises. However, tension should generally be minimized so that blood circulation will not be affected and so that the patient will not experience discomfort.

When the straps are secured to the patient and to the handle 42 or neck 46, a slight upward tension is effected to slightly raise the mouth 12 of the urinal 10 so that the base 18 is slightly angularly disposed with respect to the plane of the mattress 28 and so that the liquids within the urinal 10 will collect along the edge 31 of the urinal 10. The raising of the mouth 12 is preferably just enough (e.g., 1° or 2° from the horizontal) to permit collection of liquids along the edge 31 without misaligning the mouth 12 which is positioned to readily receive the penis of the male patient.

Figure 2:
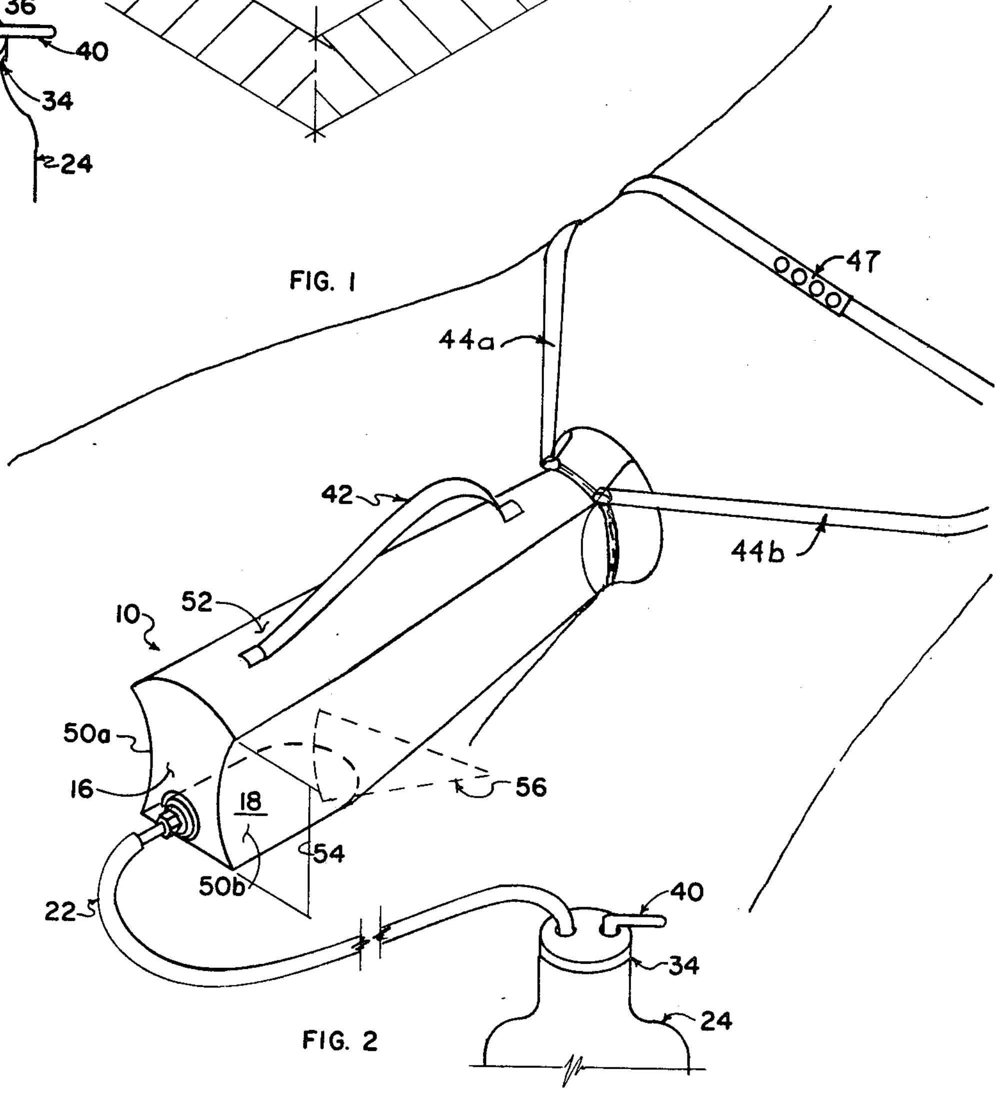
FIG. 2 is a perspective view of a preferred bed pan apparatus of the instant invention.

Referring now to FIG. 2, a preferred embodiment of the urinal 10 is shown having a substantially flat base 18, a bottom 16, opposite concave sides **50*a*, 50*b*, and a top 52. The opposite concave sides 50*a*, 50*b* are sized in height 54 and radius 56 to comfortably conform to the dimensions of the thighs of the bedridden patient. In this way the patient may not experience the discomfort of an excessively large or misshaped foreign object being positioned between his legs approximate his thighs. It should be appreciated that different sized urinals 10** may be used for male patients of different ages and sizes.

When the urinal 10 is installed with the straps **44*a*, 44*b*, it can be seen that the patient will be in position to void his bladder as desired or required without the need to continuously remove and empty the bed urinal. That is, the urine will collect in the urinal 10 and drain through the flexible hose 22 to the collecting vessel 24. The collecting vessel 24 is sized to be of sufficient volume to collect a substantial quantity of urine. It may be approximately one to two gallons in size so that it need be emptied as desired. Practically, the practice is to empty the vessel 24 at or near the end of a conventional eight hour work shift for the attending personnel (e.g., nurses) and then record volume and other diagnostic information obtainable therefrom. In this way attending personnel need not attend to the voiding needs of a bedridden non-ambulatory male patient except to empty the vessel 24** and commitantly save time and effort. Further, the patient will not need to experience any discomfort or pain because of an inability to void when required or from the use of urethetic catheter and sheaths or condoms. That is, the instant invention has been found to be markedly more comfortable and desirable in comparison with a urethetic catheter, sheath or condom. Moreover, use of the device of the instant invention has resulted in the virtual elimination of bed sores resulting from the voiding apparatus typically in use today. Further it may be noted, that for patients who have no control of their bladder or for patients who lose control of their bladder when a bed urinal is not available or in position, the labor and other difficulties associated with changing the bed linens because of the patient could not refrain from voiding is eliminated.

It is to be understood that the embodiments of the invention herein described are merely illustrative of the application of the principals of the invention. Reference herein to details of the illustrated embodiments is not intended to limit the scope of the claims which themselves recite those features regarded as essential to the invention.

I claim:

1. Apparatus for continuously collecting urine from bedridden male patients, comprising:
   - an enclosed vessel shaped and dimensioned for placement between the legs of the patient, said vessel having:
     - a substantial liquid capacity,
     - a mouth for receiving the urine of said patient and positioned with respect to said vessel to form a shoulder inhibiting the flow of liquid out from said vessel when said vessel is placed between the legs of said patient, said mouth being smaller in crosssection than said vessel and substantially larger in cross-section than the penis of a male patient,
   - an outlet adapted for connection to a drain tube, said outlet being formed in said vessel near the natural collection point of liquids when said vessel is positioned between the legs of said patient,
   - an axis and a base, said base being a substantially flat surface which is oblique to said axis and which intersects said closed end at an angle to orient the axis and in turn the mouth upward when the vessel is placed on the bed of a patient, said base being sized in area to stably support said vessel when both empty and full of liquids when in place on the bed of the patient between the legs of said patient and a substantial liquid capacity, a flaring section outward of said mouth which flares outward from said mouth and said axis, and a handle secured to said vessel;

attachment means for securing said vessel to said patient with said mouth positioned to receive the penis of said patient and with said vessel oriented upward from said bed to place said outlet at about said natural collection point of liquids, said attachment means being comprised of straps of sufficient length to be led over the thighs and around the patient at about his hips and means to secure said straps directly to said enclosed vessel and to each other at their distal ends, and wherein said straps are tensionally secured to said patient to orient said base of the vessel upward from the plane of the mattress of said bed at an angle from about one degree to about two degrees;

an enclosed collection vessel having a vent and positioned below said enclosed vessel to receive urine; and a tube to interconnect said enclosed collection vessel and said outlet and positioned to permit gravitational flow therebetween.

2. The apparatus of claim 1 wherein said outlet is positioned in said closed end at a point near the intersection of said closed end and said base.

3. The apparatus of claim 2 wherein said enclosed collection vessel is a jar adapted to receive said tube and wherein said enclosed vessel has a handle adapted to its top.

4. The apparatus of claim 3 wherein said enclosed vessel has opposite concave sides and a top, said concave sides being sized in radius and height to comfortably conform to the dimensions of the thighs of said patient.

5. The appparatus of claim 1 wherein said enclosed vessel has opposite concave sides and a top, said concave sides being sized in radius and height to comfortably conform to the dimensions of the thighs of said patient.

* * * * *